US00PP34572P2

(12) United States Plant Patent
Smith

(10) Patent No.: US PP34,572 P2
(45) Date of Patent: Sep. 13, 2022

(54) ***CHRYSANTHEMUM* PLANT NAMED 'CIFZ0091'**

(50) Latin Name: ***Chrysanthemum* x *morifolium***
Varietal Denomination: CIFZ0091

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/582,072

(22) Filed: Jan. 24, 2022

(51) Int. Cl.
*A01H 6/14* (2018.01)
*A01H 5/08* (2018.01)

(52) U.S. Cl.
USPC ..... Plt./290

(58) Field of Classification Search
USPC ..... Plt./290
See application file for complete search history.

*Primary Examiner* — Annette H Para
(74) *Attorney, Agent, or Firm* — Dale Skalla

(57) ABSTRACT

A new garden type *Chrysanthemum* plant named 'CIFZ0091' particularly distinguished by its medium size plant with mound plant habit, small to medium sized decorative flowers with yellow flower color, and a natural season response early to mid-October.

1 Drawing Sheet

Figure 1:
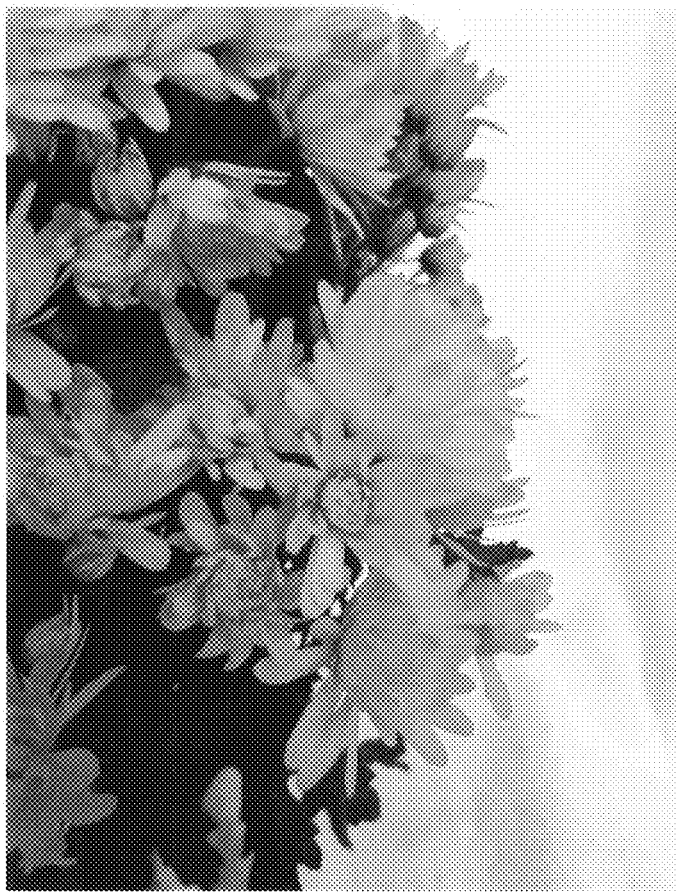

Latin name of the genus and species of the plant claimed: *Chrysanthemum* x *morifolium*.

Varietal denomination: 'CIFZ0091'.

BACKGROUND OF THE NEW PLANT

The present invention comprises a new *Chrysanthemum*, botanically known as *Chrysanthemum* x *morifolium*, and hereinafter referred to by the variety name 'CIFZ0091'.

'CIFZ0091' is a product of a planned breeding program. The new cultivar has a medium sized plant with mound plant habit, small to medium sized decorative flowers with yellow flower color, and a natural season response early to mid-October.

'CIFZ0091' originated from a cross made in February 2016 in Enkhuizen, The Netherlands. Seeds were sown in November 2016 in Gilroy, Calif. and 'CIFZ0091' was selected from the resulting population on Mar. 24, 2017 in Alva, Fla.

The female parent was 'PPP CON OR05', U.S. Plant Pat. No. 18,094

TABLE 1

Characteristics of the female parent, compared to 'CIFZ0091':

| Trait | 'CIFZ0091' | 'PPP CON OR05' |
|---|---|---|
| Natural response: | As much as 3 weeks slower | As much as 3 weeks faster |
| Blackcloth response: | Similar | Similar |
| Flower size: | Similar or a bit smaller | Similar or a bit larger |
| Flower color: | Yellow | Orange |
| Flower type: | Similar | Similar |
| Plant size: | Bit larger | Bit smaller |
| Plant habit: | Wider/more mound | Rounder |
| Flower longevity: | Initial flower color holds | Initial flower color fades quickly after opening |

The male parent was one of a few possible varieties as the seedling came from a bulked seed lot containing more than one cross. These varieties share a number of characteristics, compared to 'CIFZ0091':

TABLE 2

| Trait | 'CIFZ0091' | Unknown male |
|---|---|---|
| Natural response | Similar or two weeks slower | Similar or two weeks faster |
| Blackcloth response | Similar or one week lower | Similar or one week faster |
| Flower size: | Similar or a bit smaller | Similar or a bit larger |
| Flower color: | Yellow | Yellow or pink/ lavender |
| Flower type: | Less disc florets | More disc florets |
| Plant habit: | Similar | Similar |

The first act of asexual reproduction of 'CIFZ0091' was accomplished when vegetative stem cuttings were propagated from the initial selection in June 2017 in Alva, Fla.

BRIEF SUMMARY OF INVENTION

Horticultural examination of plants grown from cuttings of the plant initiated in January 2017 and continuing thereafter, has demonstrated that the combination of characteristics as herein disclosed for 'CIFZ0091' are firmly fixed and are retained through successive generations of asexual reproduction.

'CIFZ0091' has not been observed under all possible environmental conditions. The phenotype may vary significantly with variations in environment such as temperature, light intensity and day length.

A Plant Breeder's Right for this cultivar has not yet been applied for. 'CIFZ0091' has not been made publicly available prior to the effective filing date of this application, notwithstanding any disclosure that may have been made less than one year prior to the effective filing date of this application by the inventor or another who obtained 'CIFZ0091' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0091' with colors being as true as possible with an illustration of this type. The photographic drawings show in FIG. 1 a close view of flower of the new variety and in FIG. 2 a flowering plant from an outdoor trial.

Figure 2:
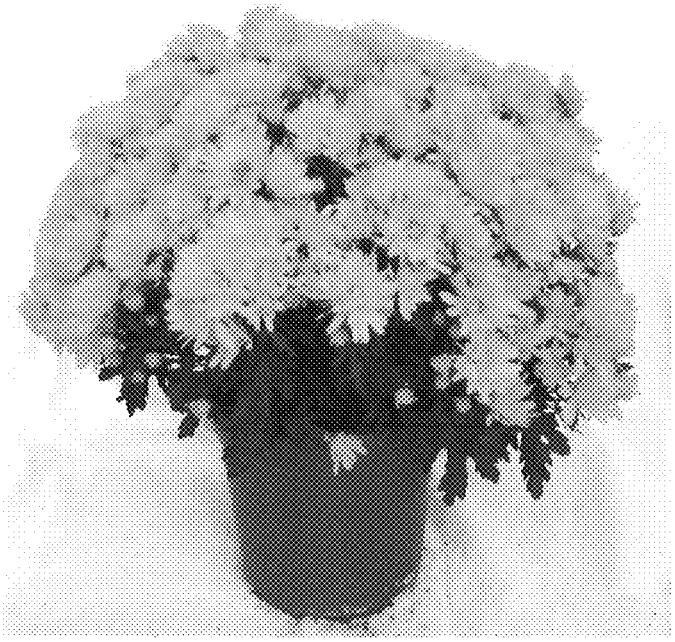

The aforementioned photographs: FIG. 1, as well as FIG. 2 were taken on Sep. 8, 2021 both showing a plant from the same blackcloth outdoor trial in Enkhuizen, The Netherlands.

These plants were about 13 weeks of age. One rooted cutting per pot had been planted in a 19 cm pot, not pinched in week 23, 2021 and black clothed from week 29. Plants started flowering the end of August 2021.

The measurements were taken in Enkhuizen, The Netherlands, in September 2021 on plants from the same outdoor blackcloth trial.

DETAILED BOTANICAL DESCRIPTION

Color references are made to The Royal Horticultural Society Colour Chart (R.H.S.) 2001.

DIFFERENCES BETWEEN THE NEW VARIETY 'CIFZ0091' AND TWO MOST SIMILAR VARIETIES

TABLE 3

| Trait | 'CIFZ0091' | 'CIFZ00034', U.S. Plant Pat. No. 29,258 |
|---|---|---|
| Natural response: | Similar except faster in the north | Similar except slower in the north |
| Blackcloth response: | 1 week faster | 1 week slower |
| Flower size: | Smaller | Larger |
| Flower color: | Similar, more golden | Similar, more yellow |
| Flower type: | Similar | Similar |
| Plant size: | Similar | Similar |
| Plant habit: | Similar | Similar |
| Flower longevity: | Less frost damage/ longer lasting | More frost damage/ shorter lived |

TABLE 4

| Trait | CIFZ0091 | 'Zanmutang', U.S. Plant Pat. No. 23,615 |
|---|---|---|
| Natural response: | Similar except with cool nights | Similar except with cool nights |
| Blackcloth response: | ½ week faster | ½ week slower |
| Flower size: | Similar or bit larger | Similar or bit smaller |
| Flower color: | Similar, bit more golden | Similar, bit more yellow |
| Flower type: | Similar | Similar |
| Plant size: | Larger | Smaller |
| Plant habit: | Similar | Similar |
| Flower longevity: | Less frost damage/ longer lasting | More frost damage/ shorter lived |

Plant:

*Form, growth and habit.*—Herbaceous garden-type, stems Upright and outwardly spreading, freely branching, strong and moderately vigorous growth habit.

*Plant height* (*above soil*).—22 cm.

*Plant height* (*inflorescence included*).—24 cm.

*Plant width.*—42 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 137A.

*Immature leaf, color lower surface.*—RHS 137B.

*Mature leaf, color, upper surface.*—RHS 137A.

*Mature leaf, color lower surface.*—RHS 137B.

*Length.*—9 cm.

*Width.*—6.0 cm.

*Shape.*—Ovate, with distinct lobes.

*Base shape.*—Attenuate.

*Apex shape.*—Abruptly acute.

*Margin.*—2-3 lobed.

*Number of margin indentations.*—Approximately 20.

*Depth of margin indentations.*—Deep.

*Leaf length terminal lobe relative to total leaf length.*—Long.

*Leaf depth lower lateral sinus.*—Short.

*Texture, upper surface.*—Bifid hairs

*Texture, lower surface.*—Bifid hairs.

*Color of veins, upper surface.*—RHS 138A.

*Color of veins, lower surface.*—RHS 138A.

*Pattern of veining.*—Palmate.

*Petiole color.*—RHS 138A.

*Petiole length.*—1.5-2.0 cm.

*Diameter.*—0.3 cm.

*Texture.*—Bifid hairs.

*Presence of stipules.*—Not present.

Stem:

*Quantity of main branches per plant.*—9.

*Color of stem.*—RHS 146B.

*Length of stem.*—9.0-10.0 cm.

*Diameter.*—0.5 cm.

*Length of internodes.*—1.5-4.0 cm.

*Texture.*—Bifid hairs.

*Color of peduncle.*—RHS 146A.

*Length of peduncle.*—3.0-4.0 cm.

*Peduncle diameter.*—0.2 cm.

*Texture.*—bifid hairs.

Inflorescence:
*Type*.—Compositae, solitary, semi-double type inflorescences borne terminally above foliage, ligulate ray florets arranged in whorls on a capitulum giving a semi-double flower.
*Quantity of short days to flowering* (*response time*).—Approximately 7 weeks.
*Quantity of inflorescences per plant*.—200 with several small buds developing.
*Lastingness of individual blooms on the plant*.—About five weeks from first color.
*Fragrance*.—Slightly spicy.
Bud (when showing color):
*Color*.—RHS 12A.
*Length*.—0.7 cm.
*Width*.—1.0 cm.
*Shape*.—Oblate.
Immature inflorescence (at moment of opening):
*Diameter*.—1.9 cm.
*Color of ray florets, upper surface*.—RHS 9A.
*Color of ray florets, lower surface*.—RHS 9B.
Mature inflorescence:
*Diameter*.—4.0 cm.
*Depth*.—2.0 cm.
*Total diameter of disc*.—0.8 cm.
*Receptacle color*.—RHS 138A.
*Receptacle height*.—0.5 cm.
*Receptacle diameter*.—1.4 cm.
*Length of corolla tube*.—0.2 cm.
Ray florets:
*Average quantity of florets*.—85 in several whorls.
*Color of florets, upper surface*.—RHS 9A.
*Color lower surface*.—RHS 9B.
*Length*.—1.8 cm.
*Width/diameter*.—0.4 cm.
*Shape*.—Oblong.
*Apex shape*.—Retuse.
*Base shape*.—Tube.
*Margin*.—entire: Small incisions may be present at tip.
*Margin*.—type of rolling: Weakly involute.
*Texture, upper surface*.—Papillate.
*Lower surface*.—Papillate.
*Ribs present*.—Yes.
*Number of keels*.—1.
*Profile at widest point*.—Flat.
*Longitudinal axis shape*.—Flat.
*Longitudinal axis curvature strength*.—No curve.
*Corolla tube shape*.—Circular.
Disc florets:
*Number of disk florets*.—50-70.
*Width*.—0.1 cm.
*Length*.—1.1 cm.
*Color*.—RHS 17A.
Inflorescence (at moment of senescence):
*Color of ray florets, upper surface*.—RHS 9A.
*Color of ray florets, lower surface*.—RHS 72B, spots 53A.
Phyllaries:
*Quantity*.—18-22.
*Color, upper surface*.—RHS 138A.
*Color, lower surface*.—RHS 138B.
*Length*.—0.7 cm.
*Width*.—0.2 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.
Reproductive organs:
*Pistil*.—One.
*Length*.—0.4 cm.
*Style color*.—RHS 5C.
*Style length*.—0.3 cm.
*Stigma color*.—RHS 9C.
*Stigma shape*.—Bi-parted.
*Ovary color*.—RHS 145D.
*Ovary length*.—0.2 cm.
*Ovary width*.—0.1 cm.
Androecium:
*Stamens*.—1, found on only disc florets.
*Color of filaments*.—RHS 157B.
*Length filaments*.—0.2 cm.
*Anther color*.—RHS 17A.
*Anther length*.—0.2 cm.
*Anther shape*.—Oval to club shaped.
*Color of pollen*.—RHS 17A.
*Pollen amount*.—Moderate.
*Fertility/seed set*.—Has not been determined to date.
*Disease/pest resistance*.—Has not been determined to date.
*Hardiness*.—Has not been determined to date.

What is claimed is:

1. A new and distinct variety of *Chrysanthemum* plant named 'CIFZ0091' substantially as illustrated and described herein.

* * * * *